United States Patent [19]
Hein

[11] Patent Number: 5,569,263
[45] Date of Patent: Oct. 29, 1996

[54] ADJUSTABLE PROVISIONAL ARTICULATING DEVICE

[75] Inventor: Todd J. Hein, Minneapolis, Minn.

[73] Assignee: Orthopaedic Innovations, Inc., Minneapolis, Minn.

[21] Appl. No.: 371,844

[22] Filed: Jan. 12, 1995

[51] Int. Cl.[6] .................................................. A61B 17/58
[52] U.S. Cl. ................................ 606/102; 606/85; 623/23
[58] Field of Search .............................. 606/102, 84, 85, 606/86, 79; 623/22, 23; 403/104, 106, 109

[56] References Cited

U.S. PATENT DOCUMENTS

| | | |
|---|---|---|
| 3,815,590 | 6/1974 | Deyerle . |
| 4,135,517 | 1/1979 | Reale . |
| 4,306,550 | 12/1981 | Forte . |
| 4,552,136 | 11/1985 | Kenna . |
| 4,601,289 | 7/1986 | Chiarizzio et al. . |
| 4,676,797 | 6/1987 | Anapliotis et al. .................. 606/79 |
| 4,787,405 | 11/1988 | Karwoski ............................ 403/109 |
| 4,963,155 | 10/1990 | Lazzeri et al. ...................... 606/85 |
| 5,100,407 | 3/1992 | Conrad et al. ...................... 606/79 |
| 5,135,529 | 8/1992 | Paxson et al. ...................... 606/85 |
| 5,397,360 | 3/1995 | Cohen et al. ....................... 623/23 |

*Primary Examiner*—Michael Powell Buiz
*Assistant Examiner*—Scott B. Markow
*Attorney, Agent, or Firm*—Janal M. Kalis

[57] ABSTRACT

The present invention relates to an adjustable provisional device for aligning a joint center distance of a joint prosthesis to a natural joint center distance. The device includes a neck having a groove and a main body with a bore for receiving the neck.

15 Claims, 4 Drawing Sheets

ADJUSTABLE PROVISIONAL ARTICULATING DEVICE

BACKGROUND OF THE INVENTION

The present invention relates to a device used in performing trial reduction in joint arthroplasty such as total hip arthroplasty.

The operation of one type of joint arthroplasty, hip arthroplasty, includes a step of removing a natural femoral head from its femoral shaft and acetabulum. In the hip arthroplasty procedure, the femoral shaft is typically rotated for better exposure. Next, a femoral shaft osteotomy is performed. In this procedure, the head is cut away from the femur.

The femoral shaft encloses an intramedullary canal, bordered by an annular femoral wall that is reamed and broached to accommodate a hip stem prosthesis. Once the annular wall of the canal has been reamed and broached, an acetabular socket component of the hip replacement prosthesis is positioned.

Preparing the femoral shaft for receiving the hip stem prosthesis has required many tools. The Forte U.S. Pat. No. 4,306,550, describes tools usable for preparing a socket and a femur for receiving a femoral prosthesis. The tools include a broach having a cutting portion and a post portion, a handle assembly with a chuck for releasably engaging the post portion to facilitate working the broach into a femur and a guide plate adapted to be journaled on the post. After a cavity is formed in the femur by use of the broach, the broach remains in the socket.

Before inserting a final femoral hip stem into the canal, a surgeon typically inserts a trial femoral stem, neck and head component in order to perform a range of motion trial. In this trial, the surgeon checks the articulation of the trial femoral component with the acetabular socket. Also, the surgeon uses trial reduction to select a proper femoral neck length in order to correct for any leg length discrepancy that a patient may display.

Previous devices used in trial reduction in hip arthroplasty have relied upon a use of a trial prosthesis with a fixed neck length which is fully inserted into the intramedullary canal of the reamed femur. This type of trial prosthesis has required many components in order to have a full array of combinations of prosthesis sizes and neck lengths.

One modification of this trial is described in U.S. Pat. No. 4,601,289 ('289). The '289 patent describes attaching a provisional head or neck onto a broach assembly. Such an attachment eliminates an extra step of inserting an additional femoral component. The attachment also reduces the quantity of components needed to make an instrumentation set. Undesirably, this type of device still requires numerous head and neck components to perform trials for all neck lengths and head combinations.

SUMMARY OF THE INVENTION

The present invention includes an adjustable provisional device for establishing a joint center distance of a joint prosthesis for trial reduction purposes. The device includes a neck having a plurality of grooves and a main body with a bore for receiving the neck.

The present invention also includes a method for adjusting neck length of a provisional prosthetic device that includes a bearing component. The method includes providing a neck component having a plurality of grooves. The method also includes providing a main body with a bore for receiving the neck component and a retaining mechanism for retaining the neck at one of the plurality of grooves. Next, the neck component is retained in the bore of the main body at one of the plurality grooves. The neck is then moved laterally to another one of the plurality of grooves.

BRIEF DESCRIPTION OF PREFERRED EMBODIMENTS

Figure 1:
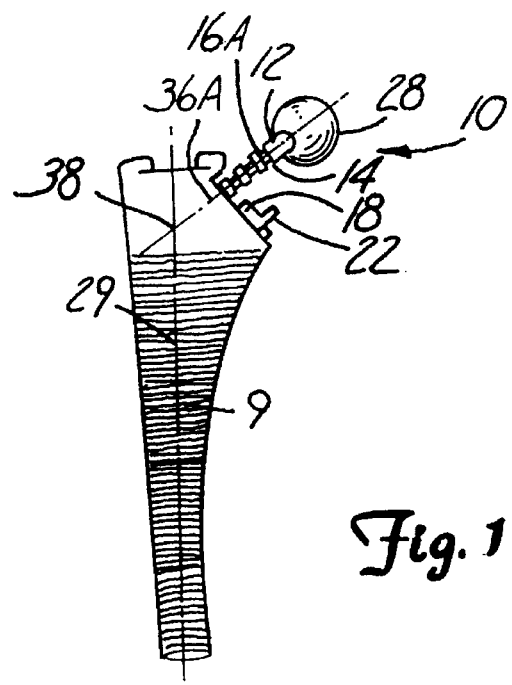
FIG. 1 is a perspective view of one embodiment of an adjustable provisional neck device of the present invention.
Figure 2:
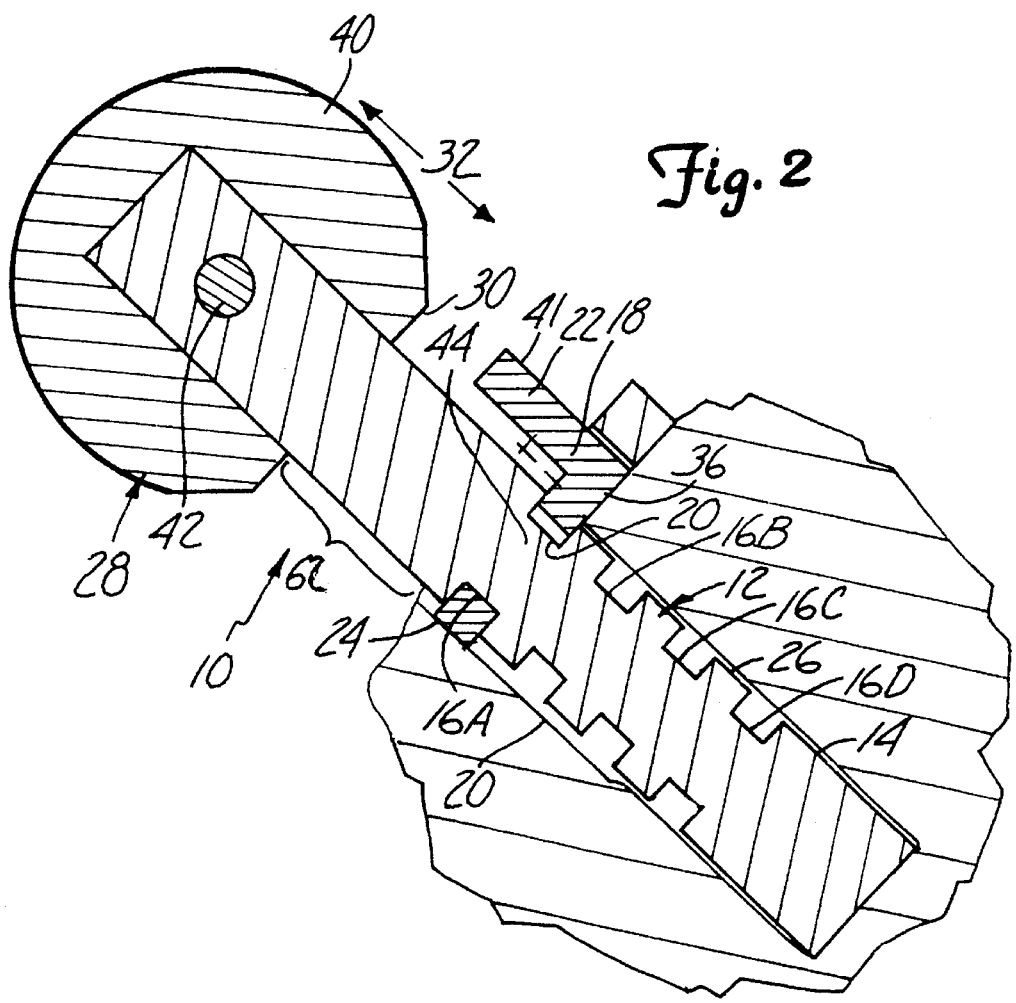
FIG. 2 is a cross-sectional view of one embodiment of the adjustable provisional neck device of the present invention.
Figure 5:
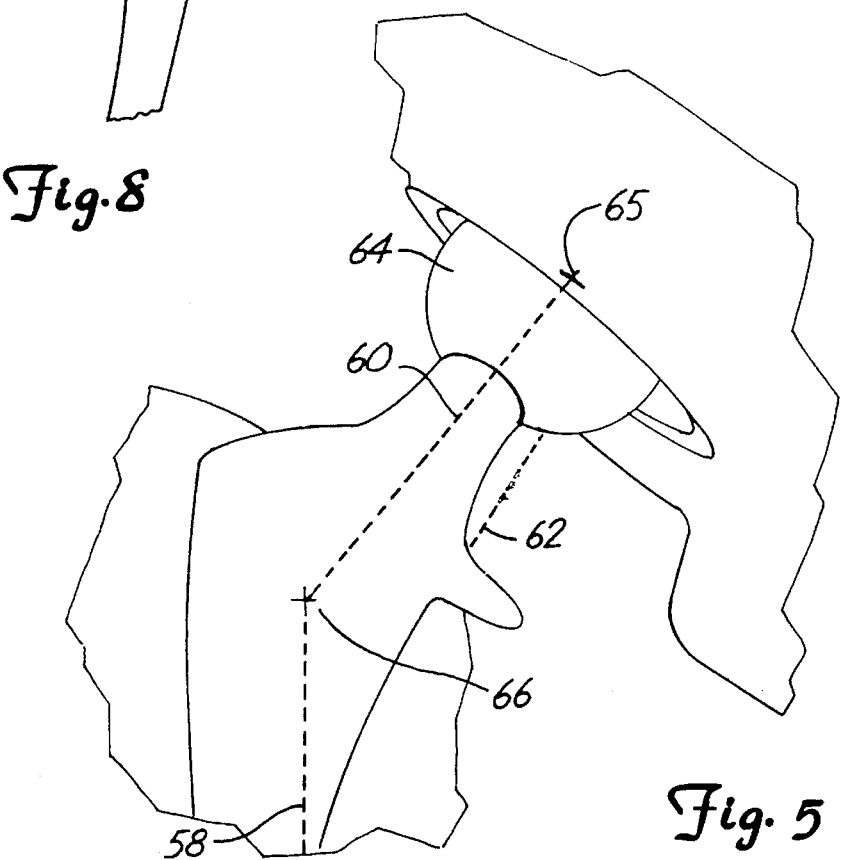
FIG. 5 shows a natural desired neck length.

A device for performing a trial reduction of a prosthetic implant generally illustrated at 10 in FIG. 1 includes a neck component 12 having an outer articulated surface 14 with a plurality of grooves 16 A, B, C, and D, illustrated in cross-section in FIG. 2, a sphere 28 positioned on the neck 12, the sphere 28 and neck 12 insertable in a broach 29. The neck 12 is retained in a bore 20 within the broach 29 by a locking mechanism 22 that includes a clasp component 24 for contacting the neck component 12 at one of the plurality of grooves 16 A, B, C and D and locking the neck component 12 in the locking mechanism 22. The neck 12 is positioned in the bore 20 so that a centerline axis 36 of the neck 12 intersects a centerline axis 9 of a prosthetic implant at a prosthetic vertex 38 as shown in FIG. 1. The alignment at vertex 38 is substantially the same as the alignment of axis 58 and 60 of a natural joint and long bone at vertex 66 as shown in FIG. 5.

The device of the present invention 10 is a great improvement over existing trial reduction devices. This is because the device of the present invention 10 does not require that a surgeon manipulate numerous components of different sizes in order to test multiple combinations to optimize a final fit of a prosthetic implant. Instead, the surgeon may use the broach 29 with a bore 20, illustrated in FIG. 2, and having an annulus 18 and locking mechanism 22 to align the neck 12 with the prosthetic implant 10 at the prosthetic vertex 38. A bearing such as a sphere may be attached to the neck 12 and aligned in accordance with a natural joint alignment as shown in FIG. 5. With the device of the present invention, a surgeon may perform the trial reduction with a single neck component 12, thereby reducing the quantity of instrument components required to perform the surgery.

In a hip arthroplasty application, the broach 29 used in trial reduction is also used to broach a femur at the intramedullary canal. Preferably, the annulus 18 is integral with the broach 29 and the bore 20 is enclosed in the broach 29.

One other advantage is that the device 10 has a versatility permitting use in conjunction with a variety of joint arthroplasty surgeries such as for hip, shoulder and knee. It is believed that the device 10 is useful for virtually any ball and socket replacement as well as hinged joint replacement and replacement of joints displaying a combination of rotation and sliding motion. The sphere 28 and neck 12 with articulating surface 14 may be sized for each of these applications. While a sphere 28 is described, it is understood that any type of prosthetic bearing is suitable for use in the present invention.

In one embodiment, illustrated in perspective at 10 in FIG. 1, the prosthetic vertex 38 is a point that is on the central axis 9 of the broach 29. The central axis 9 of the broach 29 is substantially the same as the central axis of the prosthetic implant. By "vertex" 18 is meant an intersection of a centerline of the neck 12 and a centerline of the femoral stem as shown in FIG. 5. The annulus 18 encircles the bore 20 that may be bored all the way through the broach 29.

In one embodiment, the neck component 12 has an axial cross section that is substantially circular. A lateral distance 26 separates each of the plurality of grooves 16 A, B, C and D in the articulated surface 16 of the neck 12. The lateral distance 26 is standardized with respect to neck lengths available with a particular prosthesis. The lateral distance permits a determination by incremental adjustment of the suitable distance between the sphere and prosthetic shaft. Although four grooves are shown, it is understood that the neck component 12 may have more than four grooves. It is believed that a neck 12 for use in hip surgery would have four grooves. It is believed that a neck 12 for use in knee surgery could have as many as ten grooves.

The standardization enables the surgeon to use a single neck component 12 to match an exposed distance 62 between a center 65 of a natural head 64 of a bone such as the femur of the patient and the vertex 66 as shown in FIG. 5. This distance is the "joint center distance." The neck 12 simulates a span of the distance 60 between the center of the natural head 64 and the vertex 66. In the trial reduction procedure in hip arthroplasty, the sphere 28 acts as a trial femur head.

Figure 4A:
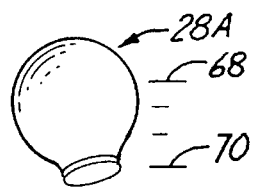
FIG. 4A is a perspective view of one embodiment of the sphere of the adjustable provisional neck device of the present invention illustrating a first sphere size.
Figure 4B:
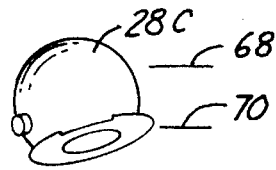
FIG. 4B is a perspective view of another sphere size of the embodiment of FIG. 4A.
Figure 4C:
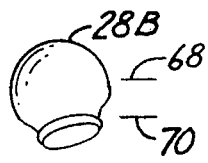
FIG. 4C is a perspective view of the embodiment of FIG. 4A, illustrating another sphere size.

Because people are of different sizes, spheres 28A–C are of different sizes as well, as shown in FIG. 4A, B, and C. However, the single neck component 12 of the present invention is usable with any of the spheres 28A, B, and C contemplated.

The sphere 28 of the device 10 with locking mechanism 22 is preferably fixedly attached to the neck 12. In the embodiment of FIGS. 1 and 2, the neck 12 and sphere 28 are a single unit. However, the neck 12 and sphere 28 may be separate units fixedly attached.

Because of the groove distance 26 standardization, the neck length exposed above the vertex 66 is readily adjustable by exposing a desired, standardized length of neck 12 between the sphere center 42 and the vertex 66 and securing the neck 12 at one of the plurality of grooves 16 A, B, C and D, with the locking mechanism 22 in the annulus 18. What is desired is that the center 42 of the sphere 28 and the prosthetic vertex 38 be separated by an exposed length of the neck Component 12, that matches the length 62 as shown in FIG. 5 for a natural femur. The length may also be adjusted to correct a leg length discrepancy in the patient.

Figure 3:
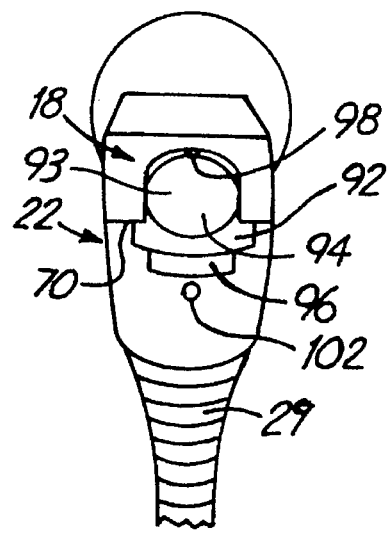
FIG. 3 is a top elevational view of one embodiment of a clasp component of the adjustable provisional neck device of the present invention.

One embodiment of the locking mechanism 22 is illustrated as an elevated view in FIG. 3. The mechanism 22 is positioned in the annulus 18. Preferably, the annulus 18 is slotted at 90 and has a U-shape as shown in FIG. 3. A movable clasp component 92 is positioned in the slot 90 of the annulus 18. The movable clasp 92 includes a hollow receiving section 94 for receiving the neck 12 and a lever 96 normal to the receiving section 94. The movable clasp 92 is held in the slot 90 at one end by a spring 98 attached to the annulus 18 and contacting the receiving section 94 of the clasp 92. The clasp component 92 is also held in place by a backstop nub 102 that prevents further movement of the clasp 92. The clasp 92 is then held in tension generated from the spring 98 by the backstop nub 102.

In a rest position, the hollow receiving section 94 of the clasp 92 is positioned so that the orifice 93 of the hollow receiving section 94 is out of alignment with the bore 20 in the broach 29. The clasp 92 is of a thickness that permits placement of the receiving section 94 within one of the plurality of grooves 16A–D in the neck 12. To position the neck 12 in the annulus 18 and bore 20 of the broach 29, the lever 96 is manually moved toward the U-shaped collar portion 90. Movement of the lever 96 puts the clasp 92 under even greater tension. Moving the lever 96 aligns the orifice 93 with the bore 20 and permits the neck 12 to be inserted through the orifice 93 and into the bore 20. Releasing the lever 96 causes the clasp section 92 to move back to the backstop nub 102 forming the backstop. The neck 12 is secured when the receiving section 94 is flush with one of the plurality of grooves 16A–D.

To release the neck 12 from the collar locking mechanism 22, the lever 96 is moved manually toward the U-shaped collar 90. Movement of the lever 96 moves the receiving section 94. The neck 12 can then be manually pulled out of the bore 20.

Figure 6:
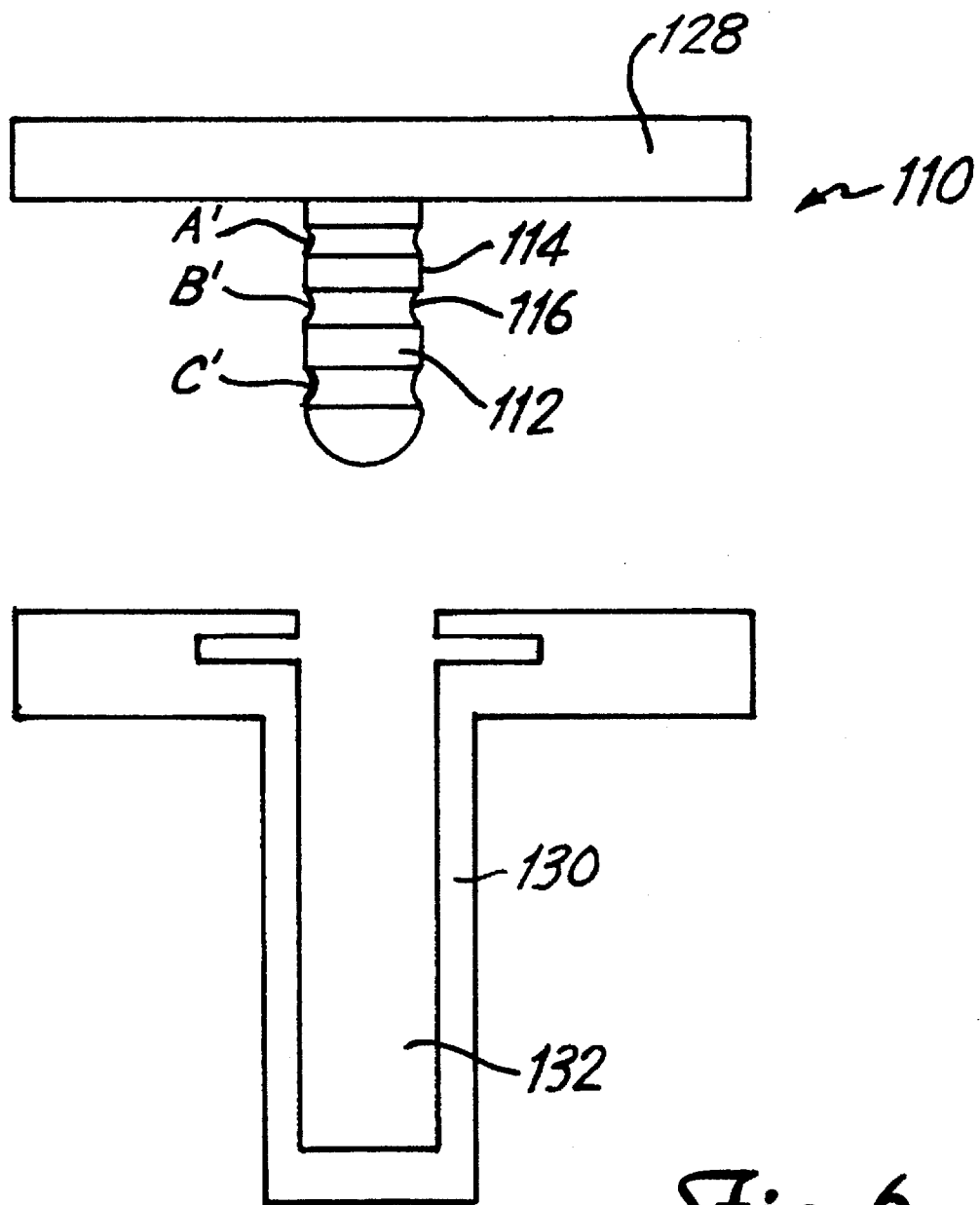
FIG. 6 shows a side view of another embodiment of the adjustable provisional neck device of the present invention.

Another embodiment of the trial reduction device of the present invention is illustrated generally at 110 in FIG. 6. This embodiment has use in performing trial reduction in knee surgery. The device includes an articulated neck 112 and a trial tibia bearing 128 attached to the neck 112. The neck 112 includes an articulated surface 114 with a plurality of annular grooves A, B, C. The plurality of grooves are separated by a standard distance as indicated at 116. The articulated neck 112 is insertable in a tibia tray 130 having a bore 132. The neck 112 may be held in position by an annulus locking mechanism 22 such as is described for the hip implant.

Figure 7:
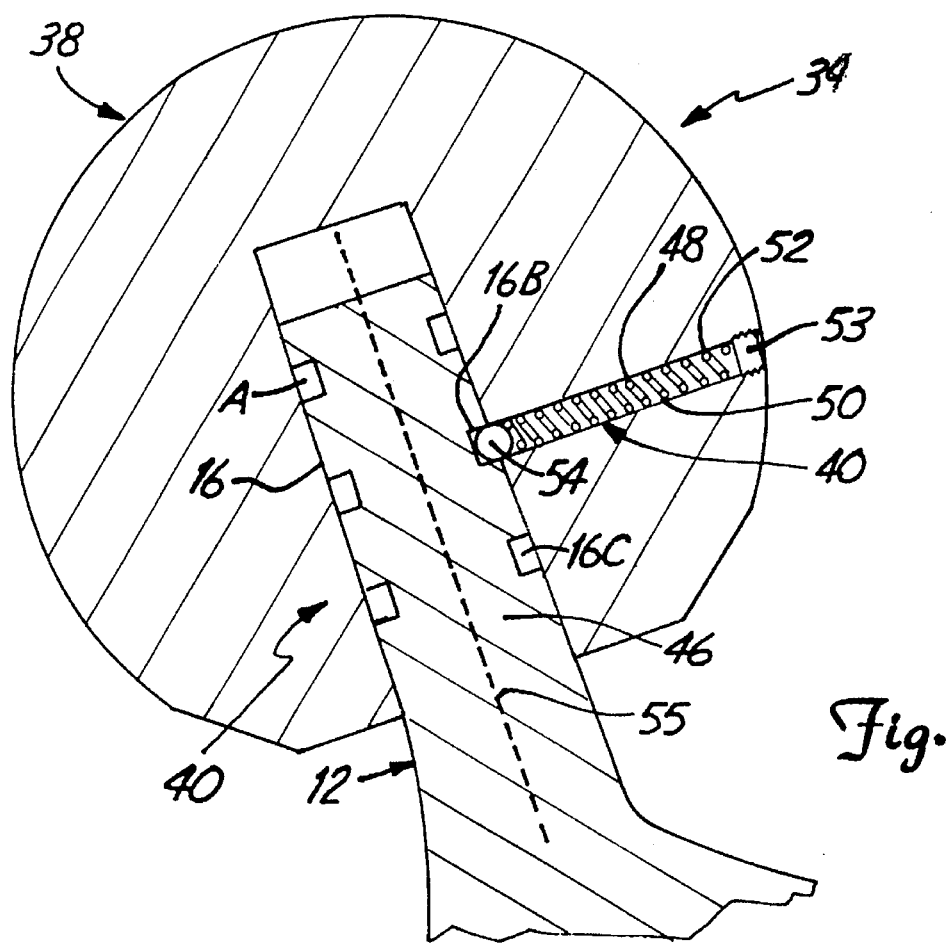
FIG. 7 shows a side view of one other embodiment of the sphere component of the present invention.
Figure 8:
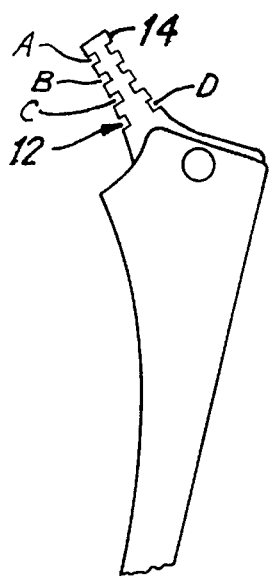
FIG. 8 shows a side view of one other embodiment of the neck component of the present invention.

Another embodiment of the trial reduction device of the present invention is illustrated generally at 34 in FIG. 7. The device 34 includes the neck component 12 having the outer surface 16 with the plurality of grooves 16A, B, and C, and a sphere 38 having a ball-type locking mechanism 40 in removable communication with the neck component 12. The sphere 38 is reversibly attachable to the neck 12 for the device embodiment 30. With the device embodiment 34, the neck component 12 may be fixedly attached to a stem component such as a broach as shown in FIG. 8.

The sphere 28C of the trial reduction device 34 has two counterbores at 46 and 48, as illustrated in FIG. 6. A sleeve 50 is positioned in the counterbore 48 and is held in place by a pin 53. A spring 52 is inserted in the sleeve 50. The spring 52 is in communication with a movable ball 54.

The neck component 12 is movable within the sphere 28C by inserting the neck 12 into the sphere 28C at the counterbore 46 and by applying a lateral force on the sphere 28C to move the sphere 28C parallel to an axis 55 of the neck 12.

When the sphere 28C is positioned so that the groove 16A of the neck 12 is in alignment with the ball 54 in counterbore 48, the ball 54 is moved into the notch 16A by inertia from the spring 50. Once in the groove 16A, the ball 54 prevents any further lateral movement of the neck 12. The range of motion test may then be performed on the patient.

To change the exposed neck 12 length, the sphere 28C is laterally movable about the neck 12. When a force is laterally applied to the sphere 28C, the ball 54 is released from its locking position in the groove 16A of the neck 12. In order for the release to occur, tension in the spring 52 should approximate inertial forces in the shaft 12 originating from lateral application of force by the surgeon.

Once the ball 54 is displaced from the groove 16A, the neck 12 can be slid to an adjacent groove such as groove 16B and locked in place when the spring 52 forces the ball 54 into the notch 16B to obtain a positive lock.

The trial reduction device has application in trial reduction of a hip stem prosthesis and a knee prosthesis. It is believed that the articulating neck device also has application in trial reduction for prosthesis of the shoulder and other joints with suitable dimensional modification in the neck 12 and sphere 28 components.

Although the present invention has been described with reference to preferred embodiments, workers skilled in the art will recognize that changes may be made in form and detail without departing from the spirit and scope of the invention.

What is claimed is:

1. An adjustable provisional device for aligning a joint center distance of a joint prosthesis to a natural joint center distance comprising:
    a bearing;
    a neck attachable to the bearing, the neck having a plurality of grooves cir comferential space apart from one another along the length of the neck; and
    a main body with a bore for receiving the neck; and
    a retaining mechanism attached to the main body for retaining the neck in the main body at one of the grooves.

2. The device of claim 1, wherein the main body is a cutting instrument.

3. The device of claim 1, wherein the main body is a broach.

4. The device of claim 1 wherein the bearing is reversibly attachable to the neck.

5. The device of claim 4 wherein the bearing has a bore for receiving the neck.

6. The device of claim 1 wherein the main body includes a clasp mechanism attached at the bore for retaining the neck at one of the grooves of the plurality of grooves.

7. The device of claim 6 wherein the clasp mechanism includes a U-shaped wafer, the water in reversible contact with the neck at a notch in the body and a spring in communication with the U-shaped wafer.

8. The device of claim 1 wherein the bearing includes a retaining mechanism for reversibly retaining the neck.

9. The device of claim 8 wherein the retaining mechanism includes a ball reversibly positionable in one of the grooves of the plurality of grooves and a spring in communication with the ball.

10. The device of claim 1 wherein the bearing is a prosthetic hip bearing.

11. The device of claim 1 wherein the bearing is a prosthetic shoulder bearing.

12. The device of claim 1 wherein the bearing is a prosthetic knee bearing.

13. A device for provisionally aligning a prosthetic bearing and a neck comprising:
    a neck component attachable to the bearing and having a plurality of grooves spaced apart along the length of the neck; and
    a main body including a bore for receiving the neck;
    a locking mechanism on the body for locking the neck to the body that includes a clasp component contacting the neck component at one of the grooves of the plurality of grooves, the clasp component including a U-shaped wafer in reversible contact with the neck, the water at a notch in the body and a spring in communication with the U-shaped wafer.

14. A method for adjustably determining neck length of a prosthetic implant comprising:
    providing a neck component wherein the neck component has a first groove and a second groove spaced along the length of the neck;
    providing a main body with a bore for receiving the neck component wherein the main body includes a clasp mechanism attached to the main body at the bore for retaining the neck at one of the grooves, wherein the clasp mechanism includes a U-shaped wafer in reversible contact with the neck at a notch and a spring in communication with the U-shaped wafer;
    retaining the neck component in the bore of the main body at the first groove; and
    moving the neck component laterally so the clasp mechanism receives the neck at the second groove.

15. An adjustable provisional device for aligning a joint center distance of a joint prosthesis to a natural joint center distance, comprising:
    a bearing;
    a neck attachable to the bearing, the neck having a plurality of spaced a part, cir cumferential grooves;
    a main body with a bore terminating an annulus for receiving the neck wherein the main body includes a clasp mechanism attached to the main body at the annulus, the clasp mechanism including a U-shaped wafer in reversible contact with the neck the wafer at the and a spring in communication with the U-shaped wafer, wherein the clasp mechanism retains the neck at one of the grooves of the plurality of grooves.

\* \* \* \* \*

UNITED STATES PATENT AND TRADEMARK OFFICE
CERTIFICATE OF CORRECTION

PATENT NO. : 5,569,263
DATED : October 29, 1996
INVENTOR(S) : Todd J. Hein

It is certified that error appears in the above-indentified patent and that said Letters Patent is hereby corrected as shown below:

Column 5:

In claim 1, line 36 between the words "of" and "grooves" insert --circumferential--;

In line 36 delete the words "cir comferential space" and insert therefor --spaced--; and In line 37 delete the word "and".

In claim 7, line 54 delete the "," and the words "the water"; and

In line 54, after the word "neck" insert --, the wafer--.

Column 6:

In claim 13, line 15, delete the word "and";

In line 16, after the ";" insert the word --and--; and

In line 21, delete "water" and insert therefor --wafer--.

UNITED STATES PATENT AND TRADEMARK OFFICE
CERTIFICATE OF CORRECTION

PATENT NO. : 5,569,263
DATED : October 29, 1996
INVENTOR(S) : Todd J. Hein

It is certified that error appears in the above-indentified patent and that said Letters Patent is hereby corrected as shown below:

In claim 15, line 48 delete the words "a part, cir cumferential" and insert therefor --apart, circumferential--;

In line 45, after the ";" insert the word --and--;

In line 49 between the words "terminating" and "an", insert the word --in--;

In line 51 after the word "neck" insert a --,--; and

In line 52 after the first occurrence of the word "the", insert the word --annulus--.

Signed and Sealed this

Twenty-third Day of September, 1997

*Attest:*

BRUCE LEHMAN

*Attesting Officer*  Commissioner of Patents and Trademarks